(12) United States Patent
Laayoun et al.

(10) Patent No.: US 9,365,894 B2
(45) Date of Patent: Jun. 14, 2016

(54) METHODS AND KITS FOR AVOIDING AMPLIFICATION OF CONTAMINATING NUCLEIC ACIDS

(75) Inventors: Ali Laayoun, La Frette (FR); Alain Troesch, Genas (FR)

(73) Assignee: BioMerieux, Marcy l'Etoile (FR)

( * ) Notice: Subject to any disclaimer, the term of this patent is extended or adjusted under 35 U.S.C. 154(b) by 99 days.

(21) Appl. No.: 13/131,174

(22) PCT Filed: Jan. 4, 2010

(86) PCT No.: PCT/FR2010/050001
§ 371 (c)(1),
(2), (4) Date: May 25, 2011

(87) PCT Pub. No.: WO2010/076546
PCT Pub. Date: Jul. 8, 2010

(65) Prior Publication Data
US 2011/0294129 A1 Dec. 1, 2011

(30) Foreign Application Priority Data
Jan. 5, 2009 (FR) ..................................... 09 50013

(51) Int. Cl.
C12P 19/34 (2006.01)
C12Q 1/68 (2006.01)

(52) U.S. Cl.
CPC .................................. *C12Q 1/6848* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 5,399,491 A | 3/1995 | Kacian et al. | |
| 6,248,522 B1 | 6/2001 | Haberhausen et al. | |
| 6,576,448 B2 | 6/2003 | Weissman et al. | |
| 2007/0238117 A1* | 10/2007 | Rajeevan et al. | 435/6 |

FOREIGN PATENT DOCUMENTS

| | | |
|---|---|---|
| EP | 0 389 063 A2 | 9/1990 |
| EP | 0569272 A1 | 11/1993 |
| EP | 1 394 173 A1 | 3/2004 |
| WO | WO 94/12515 A1 | 6/1994 |
| WO | WO 99/07887 A2 | 2/1999 |
| WO | WO 2004/067545 A1 | 8/2004 |
| WO | WO 2006/040187 A2 | 4/2006 |
| WO | WO 2006/058393 A1 | 6/2006 |
| WO | WO 2007/030882 | 3/2007 |
| WO | WO 2007/140506 A1 | 12/2007 |
| WO | WO 2008/132412 A2 | 11/2008 |

OTHER PUBLICATIONS

Corless et al., "Contamination and Sensitivity Issues with a Real-Time Universal 16S rRNA PCR," Journal of Clinical Microbiology, May 2000, vol. 38, No. 5, pp. 1747-1752.
Ashkenas et al., "Simple Enzymatic Means to Neutralize Dna Contamination in Nucleic Acid Amplification," BioTechniques, vol. 39, No. 1, Jul. 2005, pp. 69-73.
Mohammadi et al., "Optimization of Real-Time PCR Assay for Rapid and Sensitive Detection of Eubacterial 16S Ribosomal DNA in Platelet Concentrates," Journal of Clinical Microbiology, vol. 41, No. 10, Oct. 2003, pp. 4796-4798.
Delehanty et al., "RNA Hydrolysis and Inhibition of Translation by a Co(III)-Cyclen Complex," RNA, vol. 11, No. 5, 2005, pp. 831-836.
Gerber et al., "An Adenosine Deaminase that Generates Inosine at the Wobble Position of tRNAs," Science, vol. 286, Nov. 5, 1999, pp. 1146-1149.
Hayatsu, "Mutation Research/Reviews in Mutation Research," Mutation Research, vol. 659, 2008, pp. 77-82.
Shapiro et al., "Nucleic Acid Reactivity and Conformation," The Journal of Biological Chemistry, vol. 248, No. 11, Jun. 10, 1973, pp. 4060-4064.
Hayatsu et al., "The Addition of Sodium Bisulfate to Uracil and to Cytosine," Journal of the American Chemical Society, vol. 93, No. 3, Feb. 11, 1970, pp. 724-726.
Clark et al., "High Sensitivity Mapping of Methylated Cytosines," Nucleic Acids Research, 1994, vol. 22, No. 15, pp. 2990-2997.
Veedu et al., "Novel Applications of Locked Nucleic Acids," Nucleic Acids Symposium Series, 2007, No. 51, pp. 29-30.
Apr. 29, 2010 International Search Report issued in Application No. PCT/FR2010/050001 (with translation).

* cited by examiner

*Primary Examiner* — Kenneth Horlick
(74) *Attorney, Agent, or Firm* — Oliff PLC

(57) ABSTRACT

A method of amplifying a nucleic acid of interest comprises (i) treating a biological sample chemically or enzymatically to permit conversion of one type of nucleic acid base to another type of base, (ii) purifying the treated biological sample before adding amplification primers and amplification reagents to the biological sample, (iii) adding the amplification primers and amplification reagents to the biological sample, each primer being constituted of three different types of bases and being specific to a converted nucleic acid of interest or to a nucleic acid that is complementary to the converted nucleic acid of interest, and (iv) amplifying the converted nucleic acid of interest provided that the nucleic acid of interest was present in the biological sample. In the method, amplification of contaminating nucleic acids is avoided by converting the one type of nucleic acid base to another type of base prior to adding the amplification reagents to the biological sample.

25 Claims, 6 Drawing Sheets

METHODS AND KITS FOR AVOIDING AMPLIFICATION OF CONTAMINATING NUCLEIC ACIDS

The present invention relates to a method of amplification for removing contaminants in a liquid biological sample containing nucleic acids of interest that we wish to amplify, in which method the biological sample is treated to permit conversion of one of the bases of said nucleic acids of interest to another base and by introducing primers and detecting probes that are specific to the converted nucleic acids. The invention also relates to a kit for applying said method, as well as to a use of said method or of the kit for specifically amplifying and detecting bacterial, eubacterial, fungal, pan-fungal, viral or yeast targets.

Advances in molecular biology have made it possible to manipulate nucleic acids. The methods of gene amplification in vitro have now become an indispensable tool, in biological diagnostics for example, enabling a known DNA or RNA sequence to be copied in large numbers, with a multiplication factor of the order of a billion, in a relatively short time. A major drawback of these techniques is the amplification of unwanted nucleic acids, leading to erroneous results, i.e. positive results even in the absence of the target sought. These are called false positives due to contamination.

The amplification of bacterial targets by PCR (Polymerase Chain Reaction), NASBA (Nucleic Acid Sequence Based Amplification), TMA (Transcription Mediated Amplification) or any other technique for amplification of genetic material is such a sensitive technique that it requires the use of aqueous solutions, enzymes, reagents, etc., as well as plastic containers, that are free from all traces of contaminating nucleic acids. In fact, because of the sensitivity of these techniques, these contaminating nucleic acids may be amplified and may generate false positives, greatly reducing the reliability of the diagnostic test. This is true in the case of bacterial or fungal amplifications and is even more marked in pan-bacterial (also called eubacterial) and pan-fungal amplifications where the primers (and probes) used are capable of amplifying (and of detecting) the vast majority of bacterial or fungal targets. Moreover, in this particular case, most of the reagents employed in the manufacture of the amplification kits are derived from natural sources (nucleotides, enzymes, etc.) and consequently the potential risk of contamination by exogenous nucleic acids is high. Thus, in a test that is intended to evaluate the level of bacterial contamination in a biological sample, and is carried out by amplification, a positive result will be systematically generated leading to a false diagnosis because some of the enzymes used are derived from bacterial cloning and supply nucleic acids that may be amplified.

This contamination can also come from the environment and from poorly decontaminated equipment, for example: laboratory benches, personnel, equipment and pipetting devices, even plastic containers.

Some recommendations aiming to limit these contaminations have been implemented. These include preventive methods relating for example to the manipulation of the samples (notably sterilization techniques) or laboratory equipment (physically delimited work zones, use of exhaust hoods, pressure gradient between outside and inside, so that the flow always permits evacuation in the desired direction, etc.).

As already mentioned, a nonnegligible source of contamination lies in the raw materials, such as enzymes, reagents, plastic containers, actually used in the amplification reactions. Thus, Corless C. E. et al. describe the bad effects of contamination of Taq polymerase on the sensitivity of real-time PCR for detection of RNA 16S (J. Clin. Microbial.; (2000); May; 38(5): 1747-52).

A first way of correcting contamination of the enzymes required for amplification involves methods of enzymatic decontamination.

An enzymatic method, described by Ashkenas S. et al. (Biotechniques; 2005; July; 39(1): 69-73), consists of decontaminating a solution containing all of the elements necessary for an amplification. This comprises a cocktail of restriction enzymes used within the scope of RT-PCR. These enzymes degrade the double-stranded DNA present in the reaction mixture for amplification containing the target RNA to be amplified. They are then inactivated by heat when reverse transcription takes place. An alternative to this method for a PCR application, therefore in the presence of target double-stranded DNA, is also described but is limited to the use of a single type of restriction enzyme (Type IIS RE). However, the use of restriction enzymes has the drawback of only fragmenting double-stranded deoxyribonucleic acids which, moreover, must have the specific restriction site of the enzyme used. Accordingly, contaminating elements in single-stranded form and/or having few if any such restriction sites are not then removed.

Other enzymatic methods of decontamination consist of removing the undesirable nucleic acids from a solution before contacting with the nucleic acid target acids. Patent application WO-A-99/07887 describes the use of a thermolabile DNase for degrading the double-stranded deoxyribonucleic acids contained in the reaction mixture before contacting with the nucleic acid target acids. The enzyme is then inactivated by heat. The major drawback of this technique is that inactivation of this enzyme by heat in the reaction mixture requires the use of thermostable polymerases. Moreover, the reagents present in the reaction mixture may also be altered by the temperature.

The prior art also notes nonenzymatic methods for treating reagents or raw materials.

Thus, Mohammadi T. et al. (J. Clin. Microbiol.; 2003; October; 41(10): 4796-8) describe a technique consisting of column filtration of reagents for extraction and optionally for digestion by a restriction enzyme, Sau3AI, of reagents for PCR before amplification. The drawback of the filtration techniques is that these techniques cannot be applied to complex media without changing their concentration or properties. Moreover, this technique does not provide removal of the contaminating elements present on plastic containers.

Patent application WO-A-94/12515 describes a method of treating a solution containing Taq polymerase and potentially contaminating nucleic acids using a photoreactive compound. This photoreactive compound, for example a furocoumarin derivative, is activated by exposure to ultraviolet. A major drawback of this technique, apart from its restrictive application, is that it is not very efficient owing to the random degradation of said nucleic acids and it may generate fragments that can still be amplified. Another drawback of this technique is that it only decontaminates enzymatic preparations of the Taq polymerase used. The other reagents required for a process of nucleic acid amplification, such as water, buffers, plastic containers etc., must be decontaminated by some other procedure. This requires additional manipulations that are time-consuming and may be expensive.

Another nonenzymatic method described by Delehanty J. B. et al., (RNA.; 2005; May; 11(5): 831-6) employs a cobalt complex for inhibition of translation. This complex permits hydrolysis of the phosphodiester bonds of DNA and of RNA.

The major drawbacks of this technique are the incomplete degradation of the nucleic acids and the slowness of the decontamination reaction (24 hours).

Patent application WO-A-2008/132412, of the applicant, describes a method for inactivating sequences of nucleotides by means of metal chelates. A fragmentation complex, such as bis(1,10-phenanthroline)/Cu, is used for decontaminating the solutions, after the amplification stage, of all the nucleic acids present. This makes it possible to avoid contamination of new samples with amplicons resulting from a previous amplification reaction.

In the case of the first use, a major drawback of this method is that it does not really permit degradation of all of the contaminating nucleic acids, but only of the amplicons resulting from a previous amplification reaction. Another procedure will have to be used upstream and in parallel with this method for decontaminating the raw materials required for the nucleic acid amplification reaction.

Therefore there is still a need for a simple and powerful technique for treating a biological solution or liquid biological sample, for nucleic acids of interest, so that the impact of the presence of contaminants in all of the reagents, as well as on the equipment required for carrying out a nucleic acid amplification, is greatly reduced or even eliminated. This also makes it unnecessary to use the conventional techniques of decontamination of reagents and of the environment, which are very complex and often ineffective, as there is a risk of recontamination.

The inventors therefore propose an entirely new method of treatment of a solution containing nucleic acids of interest, which does not permit the direct decontamination of the amplification reagents, including the raw materials, of the amplification reaction, but makes the amplification absolutely specific to the target nucleic acids of interest present in the initial biological sample.

For this purpose, the applicant therefore proposes using a chemical or enzymatic reagent for modifying the sequence of the target nucleic acids of the biological sample in order to convert the nucleic acids of interest. This operation can be performed just before the amplification but before the reagents required for the amplification are added to permit said amplification. The stages of amplification and of detection are then performed by means of primers and of detecting probes suitable for hybridizing specifically to the converted target but not to any contaminating elements derived for example from the reagents, or from the water or from the plastic containers, etc. This method makes it unnecessary to decontaminate all of the reagents and equipment used, from extraction of the targets up to their amplification.

According to a first embodiment, the present invention relates to a method of amplification for removing contaminants in a liquid biological sample containing nucleic acids of interest that we wish to amplify, said method comprising the following stages:
 a) treating the biological sample chemically or enzymatically to permit conversion of one type of base of said nucleic acids of interest to another type of base;
 b) adding amplification primers, intended for specifically amplifying said converted nucleic acids of interest, each primer being constituted of three different types of bases;
 c) adding to the biological sample, after these treatments, the reagents necessary for the amplification, such as aqueous solution(s), solvent(s), nucleotides, enzyme(s), but also said primers previously synthesized;
 d) placing said solution and the reagents in conditions permitting amplification of the converted nucleic acids.

According to a second embodiment, the present invention also relates to a method of detection for removing contaminants in a liquid biological sample containing nucleic acids of interest that we wish to amplify and detect, said method comprising the following stages:
 a) treating the biological sample chemically or enzymatically to permit conversion of at least one type of base of said nucleic acids of interest to another type of base;
 b) adding amplification primers and detecting probe(s), intended respectively for amplifying and for detecting the amplicons resulting from amplification of the nucleic acids of interest, each primer and probe being constituted of three different types of bases;
 c) adding, to the biological sample, the reagents required for the amplification and detection, such as aqueous solution(s), solvent(s), nucleotides, enzyme(s), but also said primers and probe(s) previously synthesized;
 d) placing said solution and the reagents in conditions permitting amplification of the nucleic acids converted and detection of the amplicons generated.

Regardless of which preceding method is used, and according to a preferred embodiment of the invention, at least one purification stage is carried out between stages a) and b).

Regardless of which preceding method is used, and still according to a preferred embodiment of the invention, at least one stage of extraction of the nucleic acids contained in the liquid biological sample is carried out prior to stage a).

According to any one of the preceding instances, the amplification primers are specific to the converted nucleic acids of interest or to those complementary to them.

According to the second embodiment of the method according to the invention, the detecting probe or detecting probes are specific to the converted target and to the amplicons.

In all the preceding instances and according to a particular embodiment, the primers and/or the probes constituted of three different types of bases contain at least one modified nucleotide.

According to the last embodiment, the modified nucleotide is selected from the group comprising alpha-oligonucleotides, PNAs, LNAs, 2'-O-alkyl ribonucleotides.

According to this last embodiment, the modified nucleotide is a 2'-O-methyl ribonucleotide.

In all the preceding instances, the chemical treatment, permitting conversion of one type of base to another type of base, is effected by the action of a sulfur-containing chemical.

In all the preceding instances, the chemical agent permitting conversion of one type of base to another type of base contains a bisulfite ion ($HSO_3^-$), such as sodium bisulfite ($NaHSO_3$), ammonium bisulfite ($NH_4HSO_3$), magnesium bisulfite ($MgHSO_3$), sodium metabisulfite ($Na_2S_2O_5$), sodium hydrogen sulfite or a sulfinic acid.

According to another embodiment of the method, the enzymatic agent permitting conversion of one type of base to another type of base is a cytosine deaminase.

According to another embodiment of the method, the chemical or enzymatic treatment consists of converting one type of bases to uracils (U).

Still according to another embodiment of the method, the chemical or enzymatic treatment consists of converting cytosines (C) to uracils (U).

According to this last embodiment, the first primer, hybridizing to the converted nucleic acid of interest, is formed of adenine(s) (A), cytosine(s) (C) and/or thymines (T), and the second primer, hybridizing to the strand resulting from the elongation of said first primer, is formed of adenine(s) (A), guanine(s) (G) and/or thymines (T).

In place of the chemical agent, an enzymatic agent can be used and can permit the conversion of one type of base to another type of base; this enzymatic agent is preferably an adenosine deaminase.

According to this last, new embodiment, the enzymatic treatment consists of converting the adenines (A) to hypoxanthine.

In the case of an enzymatic agent, the first primer, hybridizing to the converted nucleic acid of interest, is formed of adenine(s) (A), cytosine(s) (C) and/or guanines (G), and the second primer, hybridizing to the strand resulting from the elongation of said first primer, is formed of cytosine(s) (C), guanine(s) (G) and/or thymines (T).

Whatever method is used, presented above, and according to a first embodiment, the amplification performed is an RT-PCR amplification.

Whatever method is used, presented above, and according to a second embodiment, the amplification performed is a PCR amplification on a single strand.

Whatever method is used, presented above, and according to a third embodiment, the amplification performed is a PCR amplification on a double strand.

In the latter case, the amplification is effected by means of two pairs of amplification primers specific to each strand of converted nucleic acid of interest.

Whatever method is used, presented above, and according to a fourth embodiment, the amplification performed is a post-transcriptional amplification, such as NASBA or TMA.

In all the instances mentioned above, the nucleic acids of interest are deoxyribonucleic acids (DNA) and/or ribonucleic acids (RNA).

The present invention also relates to a kit for carrying out the method as described above, characterized in that it comprises:
  a. an agent to permit conversion of at least one type of base of said nucleic acids of interest to another type of base;
  b. amplification primers, and optionally detecting probe(s), suitable for the converted nucleic acids of interest or the amplicons generated, these sequences being constituted of three different types of bases;
  c. reagents required for the amplification, and optionally for detection, such as aqueous solution(s), solvent(s), nucleotides, enzyme(s).

According to one embodiment of the kit, the conversion agent is selected from the group comprising sodium bisulfite ($NaHSO_3$), ammonium bisulfite ($NH_4HSO_3$), magnesium bisulfite ($MgHSO_3$), sodium metabisulfite ($Na_2S_2O_5$), sodium hydrogen sulfite or a sulfinic acid.

According to another embodiment of the kit, the agent is selected from the group comprising adenosine deaminase or cytosine deaminase.

The present invention finally relates to a use of the method as described above, or of the kit, also described above, in order to amplify and detect eubacterial and/or fungal and/or viral and/or yeast targets.

According to a variant use, the amplification primers are specific to the bacterial genus and each detecting probe is specific to at least one bacterial species.

The following terms can be used indiscriminately in the singular or in the plural.

The terms "reagent", "amplification reagent", "extraction reagent" or "purification reagent" or "raw material" denote reagents, such as reaction buffers, enzymes, monophosphate nucleosides, solvents, salts required for carrying out a reaction of extraction, of purification or of enzymatic amplification of a nucleic acid.

"Container" or "plastic container" means, in the sense of the present invention, any container such as tubes, cones or tips of pipets, whether they are of plastic (for example of the Eppendorf type) or of glass or of any other material.

"Nucleic acid" means, in the sense of the present invention, a sequence of at least two nucleotides, preferably at least ten nucleotides selected from the four types of nucleotides of the genetic code, namely:
  dAMP (deoxyadenosine 5'-monophosphate),
  dGMP (deoxyguanosine 5'-monophosphate),
  dTMP (deoxythymidine 5'-monophosphate), and
  dCMP (deoxycytidine 5'-monophosphate),
  if the nucleic acid is a DNA, or from:
  AMP (adenosine 5'-monophosphate),
  GMP (guanosine 5'-monophosphate),
  UMP (uridine 5'-monophosphate), and
  CMP (cytidine 5'-monophosphate),
  if the nucleic acid is an RNA.

The nucleic acid can also optionally comprise at least one inosine and/or at least one modified nucleotide. The term "modified nucleotide" signifies, in the present invention, a nucleotide, for example at least one nucleotide having a modified base, deoxyuridine, diamino-2,6-purine, bromo-5-deoxyuridine or any other modified base, preferably with the exception of 5-methylcytosine. The nucleic acid can also be modified at the level of the internucleotide bond for example phosphorothioates, H-phosphonates, alkyl phosphonates, at the level of the backbone for example alpha-oligonucleotides (FR-A-2,607,507) or polyamide nucleic acids (PMA) (Egholm M. et al.; J. Am. Chem. Soc.; 1992; 114; 1895-97) or 2'-O-alkyl-ribonucleotides and/or a 2'-O-fluoronucleotide and/or a 2'-amine nucleotide and/or an arabinose nucleotide, and the LNAs (Sun B. W. et al., Biochemistry; 2004; Apr. 13; 43 (14): 4160-69). Among the 2'-O-alkyl-ribonucleotides, the 2'-O-methyl-ribonucleotides are preferred, but 5-propinyl pyrimidine oligonucleotides can also be used (Seitz O., Angewandte Chemie International Edition 1999; 38(23); December: 3466-69).

The term "nucleotide" defines either a ribonucleotide or a deoxyribonucleotide.

In the sense of the present invention, "biological sample" or "liquid biological sample" means any sample that may contain nucleic acids. The latter can be extracted from a patient's tissues, blood, serum, saliva, or circulating cells, or can be derived from an agricultural or food product or can be of environmental origin. Extraction is carried out by any protocol known by a person skilled in the art.

"Contaminant" or "contaminating acid" or "contaminating nucleic acid" or "contaminating element" means, in the sense of the present invention, any nucleic acid whose amplification is undesirable and which may generate a false-positive result during detection.

The term "bisulfite" means, in the sense of the present invention, any chemical reagent whose reactive species is the bisulfite ion. A person skilled in the art will be able, for example, to use sodium bisulfite ($NaHSO_3$), ammonium bisulfite ($NH_4HSO_3$), magnesium bisulfite ($MgHSO_3$), sodium metabisulfite ($Na_2S_2O_5$), sodium hydrogen sulfite or a sulfinic acid as the chemical reagent. Preferably, the chemical reagent is sodium metabisulfite.

"Amplification" or "amplification reaction" means any technique for amplification of nucleic acids that is well known by a person skilled in the art, such as:
  PCR (Polymerase Chain. Reaction), described in U.S. Pat. No. 4,683,195, U.S. Pat. No. 4,683,202 and U.S. Pat. No. 4,800,159, and its derivative RT-PCR (Reverse Transcription PCR), notably in a one-stage format, as described in patent EP-B-0,569,272. Preferably, the PCR is performed on a single strand with a single primer pair.

LCR (Ligase Chain Reaction), disclosed for example in patent application EP-B-0,201,184, RCR (Repair Chain Reaction), described in patent application WO-A-90/01069, 3SR (Self Sustained Sequence Replication) with patent application WO-A-90/06995, NASBA (Nucleic Acid Sequence-Based Amplification) with patent application WO-A-91/02818, TMA (Transcription Mediated Amplification) with U.S. Pat. No. 5,399,491, and RCA (Rolling Circle Amplification) described in U.S. Pat. No. 6,576,448.

RT-PCR (Reverse Transcription Polymerase Chain Reaction).

In the sense of the present invention, "target" or "nucleic acid target" or "nucleic target" or "target of interest" or "nucleic acid of interest", means a nucleic acid (an oligonucleotide, a polynucleotide, a nucleic acid fragment, a ribosomal RNA, a messenger RNA, a transfer RNA) to be amplified and/or detected. The target can be extracted from a cell or synthesized chemically. The target can be free in solution or can be bound to a solid support.

The term "solution" denotes a homogeneous or heterogeneous aqueous solution.

"Solid support" means particles, which can be of latex, glass (CPG), silica, polystyrene, agarose, sepharose, nylon, etc. These materials can optionally permit encapsulation of magnetic material. It can also be a filter, a film, a membrane or a strip. These materials are well known by a person skilled in the art.

The target can be a viral, bacterial, fungal, or yeast nucleic acid, present in a mixture, in the form of a single or double strand of DNA and/or of RNA. In general, the target is of a length between 50 and 10 000 nucleotides, but most often it is between 100 and 1000 nucleotides.

The term "natural target", called CNT, denotes in the sense of the present invention a target nucleic acid to be amplified composed of a nucleotide sequence of at least four nucleotides whose bases are of four different types and are selected from the group: adenine, guanine, cytosine and thymine (for DNA) or uracil (for RNA). Optionally, modified nucleotides as described previously can be present. Of course, the so-called natural primers permitting amplification of CNT are called PNT1 and PNT2. If there are several amplifications in parallel, the primers will be called PNT1a and PNT2a for the first pair and PNT1b and PNT2b for the second pair, for example.

The term "converted target" or "four-base target", called C4B, means that the target or the target nucleic acid has been treated with a chemical or enzymatic agent permitting conversion of one type of base carried by a nucleotide to another different type of base. The number and the sequential order of the nucleotides are not changed by the action of the agent. The converted target nucleic acid (C4B) therefore has the same total number of nucleotides as the unconverted target nucleic acid (CNT) but is constituted of a nucleotide sequence in which at least one type of base has been changed to another type of base. Preferably, the converted target will be constituted of a nucleotide sequence of the type with bases selected from the group comprising adenine, thymine, guanine, uracil, cytosine and hypoxanthine.

The four-base target can therefore be a target nucleic acid to be amplified, which has been converted by bisulfite, i.e.:
the adenine, guanine and thymine are unchanged but the cytosine is converted to uracil (for DNA).
the adenine, guanine and uracil are unchanged but the cytosine is also converted to uracil (for RNA). In this case, the conversion will make it possible to obtain a converted target with three bases, the uracils that are naturally present remaining unchanged and the cytosines being converted to uracils. This RNA will be constituted of a nucleotide sequence constituted of three types of bases only, i.e. adenine, guanine and uracil.

To simplify the terminology used, the term C4B will be used for the converted DNA targets (four bases), but also for the converted RNA targets (three bases). In any case, this does not affect the amplification of the target nucleic acid starting from C4B, by means of specific primers called P3B1 for the upstream primers and called P3B2 for the downstream primers, the amplicon C3B always having three bases (see below). Once again, in the case of a multiplex amplification, the specific primers will be called P3B1a and P3B1b for the upstream primers, and will be called P3B2a and P3B2b for the downstream primers.

This conversion can apply to cytosine deaminase, in which case:
the adenine, guanine and thymine are unchanged but the cytosine is converted to uracil (for DNA).
the adenine, guanine and uracil are unchanged but the cytosine is also converted to uracil (for RNA) (cf. patent EP-B-1,654,388). In this case, conversion will make it possible to obtain a converted target with three bases, the uracils that are naturally present remaining unchanged and the cytosines being converted to uracils. This RNA will be constituted of a nucleotide sequence constituted of three types of bases only, i.e. adenine, guanine and uracil. Once again, to simplify the terminology used, the term C4B will also be used for the converted RNA targets. In any case, this has no effect on amplification of the target nucleic acid from C4B, by means of specific primers called P3B1 for the upstream primers and called P3B2 for the downstream primers, the amplicon C3B still having three bases (see below).

This conversion can apply to adenosine deaminase, in which case:
the cytosine, guanine and thymine are unchanged but the adenine is transformed to hypoxanthine (for DNA).
the cytosine, guanine and uracil are unchanged but the adenine is transformed to hypoxanthine (for RNA).

We may mention in this connection the document Gerber A. P. et al. Science; 1999; Nov. 5; 286 (5442): 1146-49.

The term "three-base target", called C3B, denotes in the sense of the present invention a target nucleic acid amplified from C4B, as reference, and by means of specific primers called P3B1 for the upstream (or "forward") primers, and called P3B2 for the downstream (or "reverse") primers, defined below.

The term "type of base" defines the nature of the base, i.e. either adenine (A), or thymine (T), or cytosine (C), or guanine (G), or uracil (U), or hypoxanthine, despite the fact that they are associated with ribose (optionally substituted, for example by the presence of a 2'-O-methyl group) and optionally with one, two or three phosphate groups.

"Three-base primer", called P3B1 and P3B2, means in the sense of the present invention a single-stranded nucleotide sequence constituted of a sequence of at least three nucleotides, modified or not, constituted of three different types of bases selected from the group comprising adenine, thymine, guanine, cytosine. The three-base sense primer (P3B1) is complementary to at least a part of the sequence of converted target nucleic acid (C4B) or to at least a part of the nucleotide sequence of the nucleic acid synthesized starting from the antisense primer (amplicon) and serves as the point of initiation of synthesis of a nucleic acid in the presence of amplification reagents. The antisense three-base primer (P3B2) is complementary to at least a part of the nucleotide sequence of the nucleic acid synthesized from the sense primer. These primers are of a size between 10 and 100 nucleotides, preferably between 12 and 50 and even more preferably between 15 and 30 nucleotides.

Depending on the amplification technique employed, the primer can comprise, in addition to the sequence of hybridization to the converted target, the nucleotide sequence of a promoter (for example T3, T7 or SP6) in the case of post-transcriptional amplification, of the NASBA or TMA type. It is well known by a person skilled in the art that in the case of these post-transcriptional amplifications, the primer will be constituted of a part of a sequence whose nucleotide sequence will be composed of nucleotides of four different types of bases (promoter sequence) and of a sequence whose nucleotide sequence will be composed of nucleotides of three different types of bases (sequence permitting hybridization of the primer to the converted target).

"Detecting probe" or "probe", called SNT, means a nucleic acid sequence of a nucleotide sequence of four bases of different types selected from the group comprising adenine, thymine, guanine, uracil, cytosine, which is capable of hybridizing specifically to an amplicon and bears at least one marker. The probe can be a probe of rounded form (called O-probe, see the patent application of the applicant FR08/54549 filed on 4 Jul. 2008), a molecular beacon, a Taqman® probe or a FRET probe. These last three types of probes are well known by a person skilled in the art. These probes can optionally be constituted completely or partially of modified nucleotides. Each probe has a marker and optionally a quencher.

"Marker" means a molecule carried by a nucleotide. The bond between the marker and the nucleotide can be effected in various ways known by a person skilled in the art. Manual coupling is carried out using markers bearing an activated group, typically a carboxyl or a thiol, which are coupled to a modified internal nucleotide bearing the corresponding reactive group (amine or thiol, for example), or to one end of the nucleotide strand modified with these same reactive groups. Automatic coupling is carried out using phosphoroamidites bearing the marker, and then coupling takes place during automated synthesis of the nucleotide strand, either to one end of the strand, or to an internal position, depending on the type of phosphoroamidite used. The marker can be a fluorophore or a fluorescence quencher.

"Fluorophore" means a molecule that emits a fluorescence signal when it is excited by light of a suitable wavelength. The fluorophore can notably be a rhodamine or a derivative such as Texas Red, a fluorescein or a derivative (for example FAM), a fluorophore of the Alexa family such as Alexa 532 and Alexa 647, Alexa 405, Alexa 700, Alexa 680, Cy5 or any other fluorophore that is suitable, depending on the measuring instrument used. The fluorophores available for the detecting probes are very varied and are known by a person skilled in the art.

In the sense of the present invention, "fluorescein" means an aromatic chemical molecule that emits a fluorescence signal with an emission maximum around 530 nm, when it is excited by light at a wavelength in the region of 490 to 500 nm, preferably of 495 nm.

"Fluorescence quencher" or "quencher" means a molecule that interferes with the fluorescence emitted by a fluorophore. This quencher can be selected from nonfluorescent aromatic molecules, to avoid parasitic emissions. Preferably, said quencher is a Dabsyl or a Dabcyl or a "Black hole quencher™" (BHQ), which are nonfluorescent aromatic molecules that prevent the emission of fluorescence when they are physically in the proximity of a fluorophore. The fluorescence resonance energy transfer (FRET) technique can also be used, as described for example in Fluorescent Energy Transfer Nucleic Acid Probes, p. 4, Ed. V. V. Didenko, Humana Press 2006, ISSN 1064-3745. The quencher can also be selected from fluorescent molecules, for example TAMRA (carboxytetramethylrhodamine).

The "three-base detecting probe" or "three-base probe", called S3B, is a probe as defined previously and which in addition to the preceding characteristics is constituted of a nucleotide sequence of three different types of bases selected from the group comprising adenine, thymine, guanine, cytosine. It will be readily understood by a person skilled in the art that depending on the forms of the probes (Beacon, O-probe, etc.), the probe will be constituted of a part of a sequence whose nucleotide sequence will be composed of nucleotides with four different types of bases and of a sequence whose nucleotide sequence will be composed of nucleotides with three different types of bases (sequence permitting hybridization and detection of amplicons).

In certain cases, to improve hybridization to the amplicons and therefore detection thereof, the probes according to the invention can if necessary contain uracil in place of thymine. In this case, the probes according to the invention will be constituted of a nucleotide sequence with four different types of bases (uracil, guanine, adenine, thymine). To simplify the terminology used, the term "three-base probes" or S3B will also be used for probes of this type for which better hybridization is required. In any case, this does not affect detection of the C3B amplicons and/or of the complementary strand, C3Bc, the C3B and C3Bc amplicons always having three bases (see above).

For better understanding of the principle of the invention, we shall take as an example the target whose hypothetical sequence is as follows (SEQ ID No. 1), which corresponds to CNT. Within the scope of conversion with bisulfite, the 4-base targets, 3-base targets and primers and probes will have the following sequences:

```
CNT:  5'-ATCGAAATTTCCCGGGATCG-3',      SEQ ID No. 1

C4B:  5'-ATUGAAATTTUUUGGGATUG-3',      SEQ ID No. 2

P3B1: 3'-TAAC-5',                      SEQ ID No. 3

C3B:  3'-TAACTTTAAAAAACCCTAAC-5',      SEQ ID No. 4

P3B2: 5'-ATTG-3',                      SEQ ID No. 5
and

S3B:  3'-AAAAAA-5',                    SEQ ID No. 6
```

C3B therefore has as complementary C3Bc:

```
C3B:  3'-TAACTTTAAAAAACCCTAAC-5',     SEQ ID No. 4

C3Bc: 5'-ATTGAAATTTTTTGGGATTG-3',     SEQ ID No. 7
``` which is completely different compared to CNT:

```
CNT: 5'-ATCGAAATTTCCCGGGATCG-3',    SEQ ID No. 1
C3Bc: 5'-ATTGAAATTTTTTGGGATTG-3',   SEQ ID No. 7
```

"Hybridization" means the process during which, in suitable conditions, two single-stranded nucleotide fragments, having completely or partially complementary sequences, are able to form a double strand or "duplex" stabilized by hydrogen bonds between the nucleic acid bases. The hybridization conditions are determined by stringency, i.e. the rigor and low salinity of the operating conditions. Hybridization is increasingly specific when it is carried out with greater stringency. Stringency is notably defined as a function of the composition of bases of a probe/target duplex, as well as by the degree of mispairing between two nucleic acids. Stringency can also be a function of the reaction parameters, such as concentration and type of ionic species present in the hybridization solution, nature and concentration of denaturants and/or hybridization temperature. The stringency of the conditions in which a hybridization reaction must be carried out will depend mainly on the hybridization probes used. All these data are well known and the appropriate conditions can be determined by a person skilled in the art.

The term "Ceq" defines a cell-equivalent, a unit used in a eubacterial PCR amplification and which corresponds to 1000 copies of a DNA. A cell can contain about $10^3$ copies of RNA 16s (target of the eubacterial primers and probes).

The examples and the appended figures represent particular embodiments and are not to be considered as limiting the scope of the present invention.

FIG. 1 shows the advantage of employing a stage of conversion of a nucleic acid target by sodium bisulfite prior to its amplification. If the amplification is performed conventionally, i.e. with natural targets (unconverted, called natural or CNT in the figure) and using normal nucleotide primers (called PNT1 and PNT2 in the figure), the contaminating elements naturally present in the amplification mixture are then co-amplified optionally with the target of interest. Conversely, if the target is converted before amplification, called C4B in the figure, and amplification is performed using three-base nucleotide primers, called P3B1 and P3B2, designed for the converted target, only this specific target will be amplified and detected. Although still present in the solution, the contaminants cannot be amplified. In fact, the primers according to the invention, three-base primers P3B, cannot hybridize to the contaminating nucleic acids that have nucleotides with four different types of bases, even nonspecifically. The amplification reaction gives amplicons called C3B in the figure, starting from the converted target C4B, then C3Bc for the strand complementary to C3B. The invention is of quite particular advantage for amplifications (NASBA, PCR, RT-PCR, TMA, etc.) of bacterial, eubacterial, fungal, pan-fungal, viral or yeast targets.

FIG. 2 describes the chemical reaction that permits conversion of the cytosine base to the uracil base (according to Hayatsu H.; Mut. Research; 2008; 659: 77-82).

FIG. 3 shows analytical spectra of the composition of a DNA by mass spectrometry with electrospray ionization (ESI). The analysis was carried out on a DNA target before (a) and after (b) conversion by sodium bisulfite. The abscissa shows the time in minutes and the ordinate shows the absorbance in arbitrary units. The value M+H represents the molecular weight of a molecule to which the mass of one mole of proton is added. For example, the presence of deoxycytosine is demonstrated by the appearance of a mass corresponding to this molecule.

FIG. 4 is a comparison of negative controls in eubacterial NASBA amplification (the target is replaced with water) performed with different types of amplification primers (PNT or P3B as defined previously). Detection of the amplicons is effected in real time by measuring the fluorescence at 488 nm in arbitrary units (RFU for relative fluorescence unit) on the ordinate; the abscissa shows elapsed time in minutes. Experimental conditions (a) correspond to amplification and detection of the negative control with primers (PNT) and a natural detecting probe (SNT). Experimental conditions (b) correspond to amplification and detection of the negative control with three-base primers (P3B) and a three-base detecting probe (S3B).

Figure 6A:
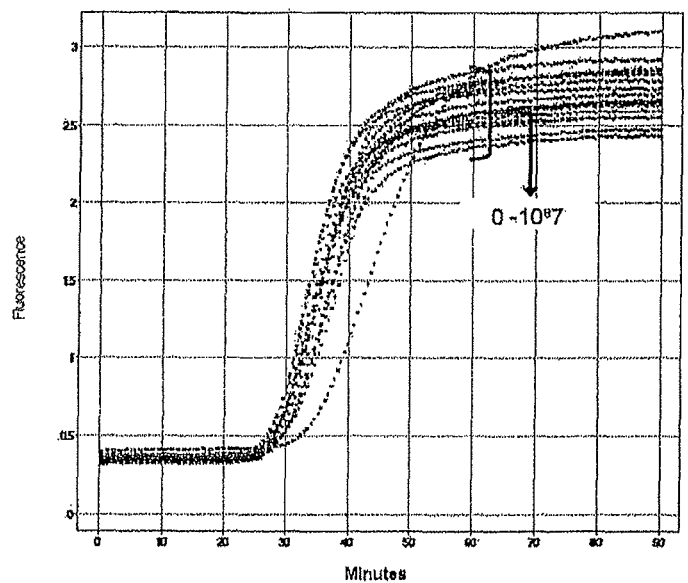
FIG. 6 shows a comparison of dilution series of targets in eubacterial NASBA amplification. Detection of the amplicons is effected in real time by measuring the fluorescence at 488 nm (in arbitrary units RFU, on the ordinate) as a function of time (minutes, abscissa)

FIG. 6A: Amplification (primers PNT) and detection (probes SNT) of a dilution series ranging from 0 to $10^{e}7$ copies of a synthetic target composed of four different types of bases (CNT).

Figure 6B:
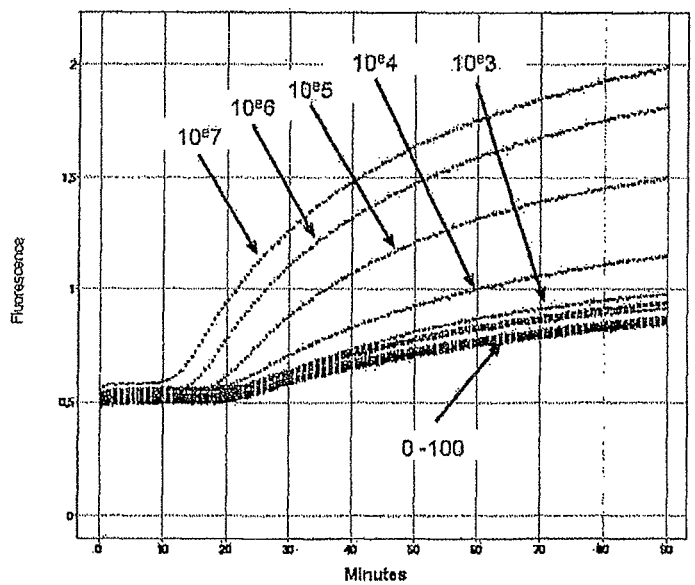

FIG. 6B: Amplification (primers P3B) and detection (probes S3B) of a dilution series ranging from 0 to $10^{e}7$ copies of a synthetic target composed of three different types of bases (C3Bc).

Figure 7A:
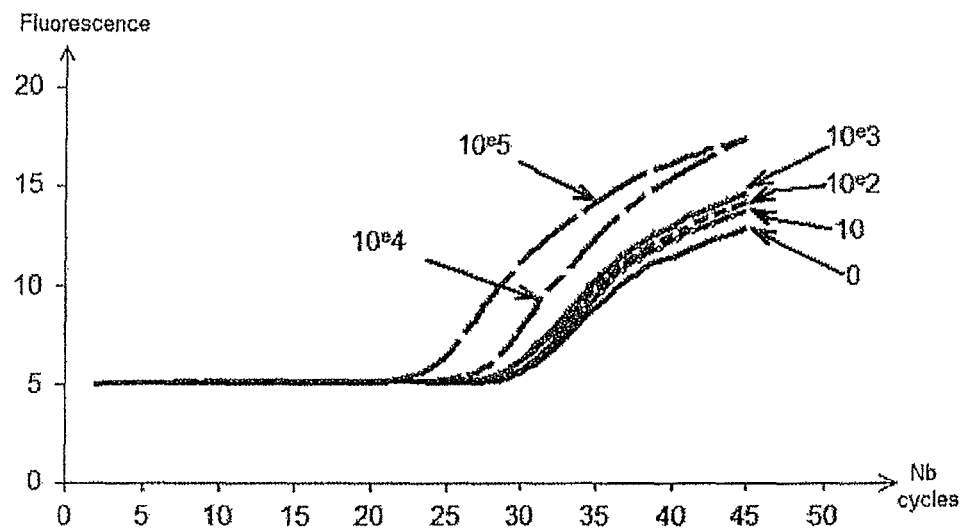

FIG. 7 shows a eubacterial PCR amplification. Detection of the amplicons is effected at each end of cycle by measuring the fluorescence at 488 nm (in arbitrary units RFU). The abscissa shows the cycle number and the ordinate shows the fluorescence in arbitrary units, with:

FIG. 7A: Amplification (primers PNT) and detection (probes SNT) of a dilution series ranging from 0 to $10^{e}5$ copies of a synthetic target composed of four different types of bases (CNT).

Figure 7B:
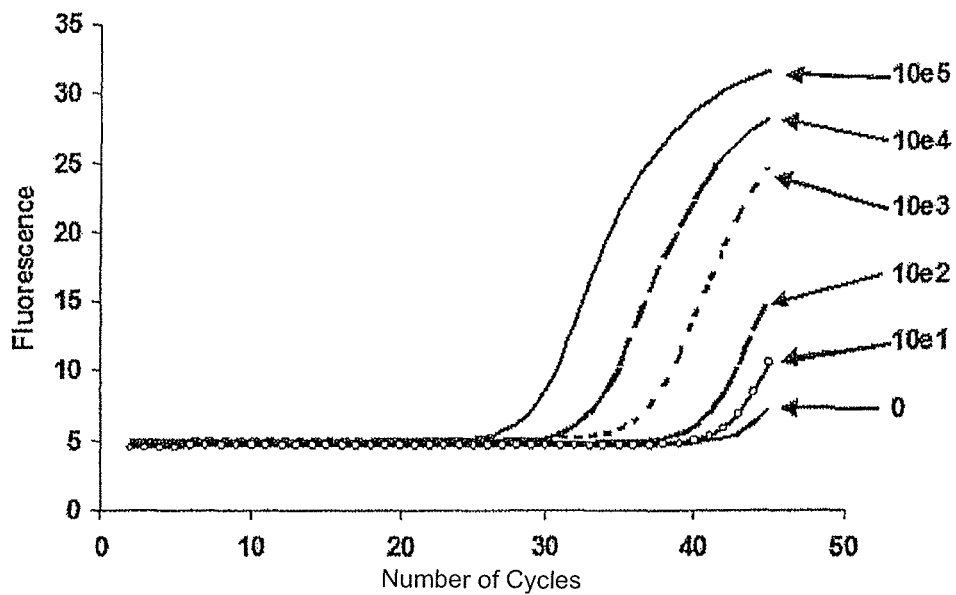

FIG. 7B: Amplification (primers P3B) and detection (probes S3B) of a dilution series ranging from 0 to $10^{e}5$ copies of a synthetic target composed of three different types of bases (C3Bc).

Figure 8A:
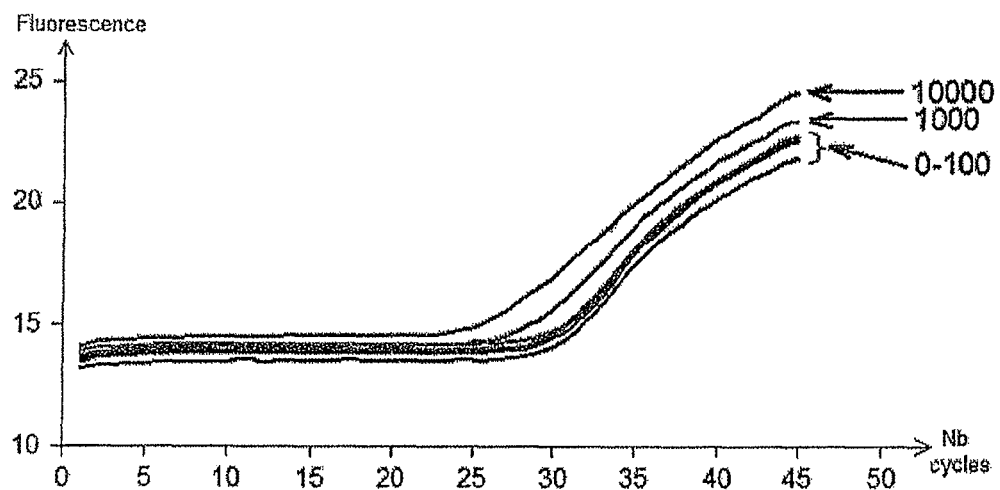

FIG. 8 is a eubacterial PCR amplification of a dilution series of gDNA of *Escherichia coli*. Detection of the amplicons is effected at each end of cycle by measuring the fluorescence at 488 nm, as already mentioned. The abscissa shows the cycle number and the ordinate shows the fluorescence in arbitrary units as described previously:

FIG. 8A: Amplification (primers PNT) and detection (probes SNT) of a dilution series ranging from 0 to $10^{e}5$ copies of gDNA of *Escherichia coli* (CNT).

Figure 8B:
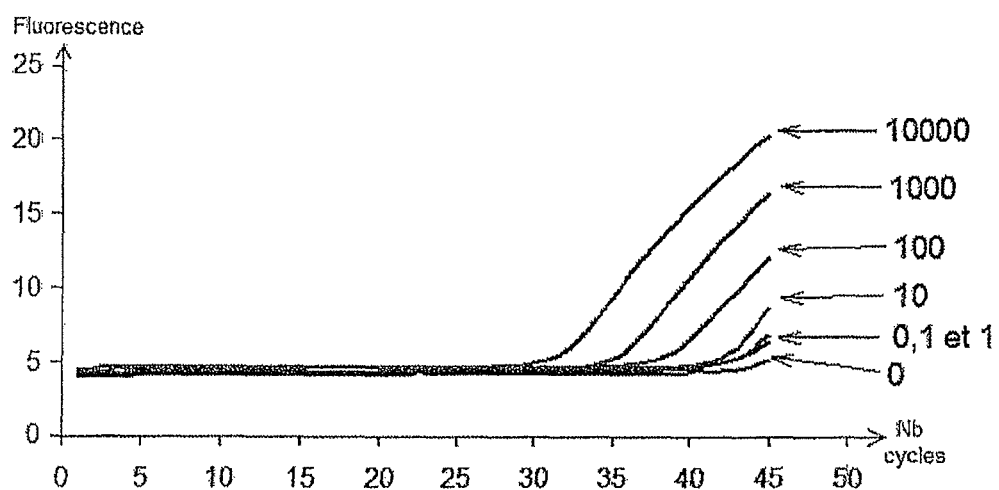

FIG. 8B: Amplification (primers P3B) and detection (probes S3B) of a dilution series ranging from 0 to 10e5 copies of gDNA of *Escherichia coli* converted by treatment with bisulfite (C4B).

Figure 1:
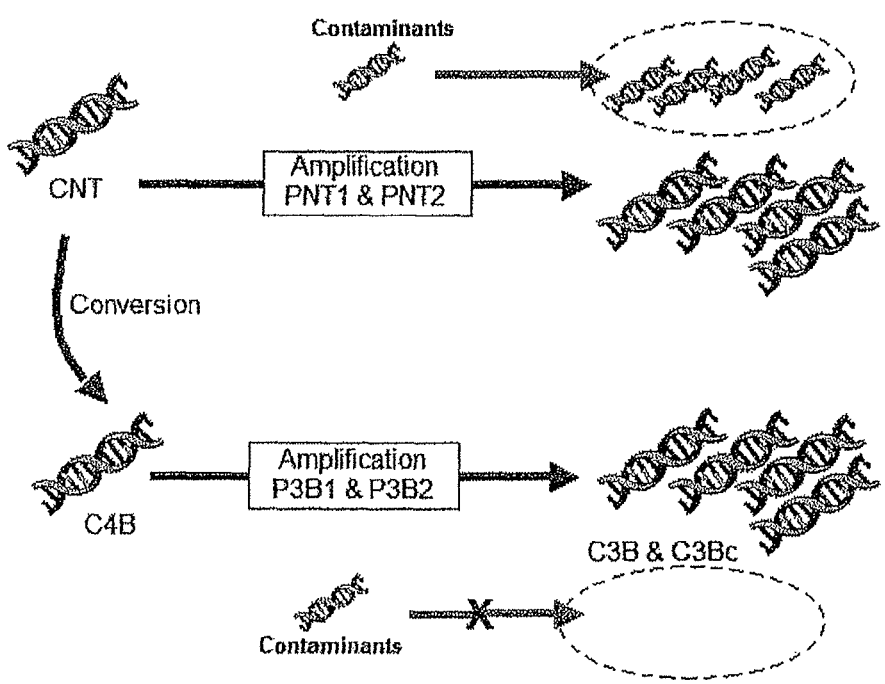
Figure 2:
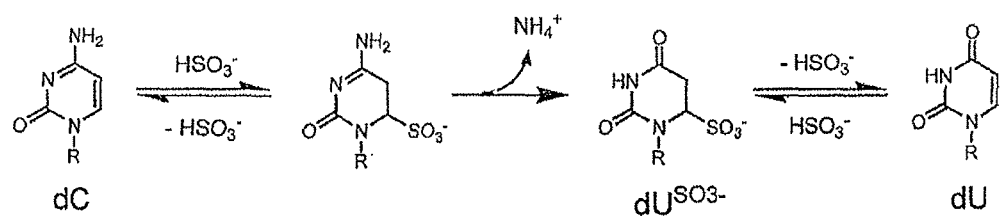

Referring to FIGS. 1 and 2, more precisely, conversion of the target by sodium bisulfite is performed as follows. It is a protocol comprising four stages:

(1) Firstly, conversion begins with denaturation of the target with sodium hydroxide (NaOH) then addition of sodium bisulfite and hydroquinone (the latter can limit oxidation of the bisulfite).

(2) The target is then purified by column filtration.

(3) The target is desulfonated in a basic medium.

(4) Finally a last column purification gives a converted target ready to be amplified.

Chemical conversion of nucleic acids by means of bisulfite is already known in the prior art. Regarding this, the following are found:

1) Very early works by Shapiro and by Hayatsu including, among others:

"Reaction of Cytosine and Uracil with sodium bisulfite" Shapiro R. et al., J. Biol. Chem.; 1973; June; 248: 4060-64, and "The addition of sodium bisulfite to uracil and to cytosine" Hayatsu H. et al., J. Am. Chem. Soc.; 1970; 40(26): 724-26.

This proves that many documents have been published in this area but without really defining, at that time, the implications that there would be in diagnostics.

2) Patent applications concerning the technique of treatment of DNA with bisulfite for using a group of non-degenerate primers in order to amplify a set of nucleic acids belonging to one and the same original species:

bacterial (WO-A-2006/058393 and WO-A-2007/140506), and viral (WO-A-2007/030882).

3) An improvement of the method of treatment of nucleic acid with bisulfite for detecting the methylation motifs of genomic sequences of DNA "High Sensitivity mapping of methylated cytosines" by Clark S. J., Nucleic. Acids Res.; 1994 Aug. 11; Vol. 22 (15): 2990-97.

4) A new development of a method of treatment of a nucleic acid with bisulfite, the treatment being adapted to nucleic acids fixed on solid supports (EP-B-1,590,362 and EP-A-1,394,173).

5) A publication that summarizes the state of the art of the treatment of a nucleic acid with bisulfite for sequencing genomic DNA and identification of methylated cytosine motifs. This synopsis was written by the developer of the bisulfite technology: Hayatsu H., Mut. Research; 2008; 659: 77-82.

It is therefore clear that the chemistry of conversion using bisulfite was already well described more than thirty-five years ago. In contrast, the chemical or enzymatic conversion used in order to remove contaminating nucleic acids due to the reagents used during extraction, purification and amplification of a target nucleic acid is certainly not described or even mentioned.

Our invention therefore relates to specific amplifications of the converted target without background noise due to the contaminating nucleic acids.

The objective is therefore to provide a method having the following advantages:

1) simple and quick,
2) usable just before the stage of amplification,
3) capable of converting the target at high yield,
4) compatible with numerous amplification techniques including PCR, as well as so-called post-transcriptional amplifications (NASBA and TMA).
5) can be automated and can be adapted to a solid and/or magnetic support.

EXAMPLE 1

Demonstration of Conversion of a Nucleic Acid Target by Bisulfite

Objective:

To demonstrate the conversion by bisulfite of a biological target having the four types of bases A, T, G, C, that is A (for Adenine), T (for Thymine), G (for Guanine) and C (for Cytosine) to a target with four bases A, T, G and U (for Uracil).

Procedure:

The conversion is performed with the commercial kit ZYMO-EZ DNA Methylation-Gold™ Kit, ZYMO Research, #D5005 (Orange, Calif. 92867—United States of America), following the protocol supplied with the kit.

The target to be converted is a commercial sample of genomic DNA extracted from the bacterium *Escherichia coli* O157, #IRMM449-1EA, Sigma-Aldrich Chimie (L'Isle d'Abeau Chesnes—FRANCE) of 500 to 4000 double-stranded nucleotides.

Conversion by Bisulfite:

The protocol of the kit is followed, according to which 130 μl of CT Conversion Reagent present is added to 20 μl of sample (which corresponds to 200 ng of genomic DNA extracted from *Escherichia coli*). The mixture is incubated for 10 minutes at 98° C., for denaturation of the targets of the genome of *Escherichia coli*, then for 150 minutes at 64° C. and 5 minutes at 4° C. (Thermocycler Applied Biosystems GeneAmp 9700, Foster City, U.S.A.). This gives a solution containing a converted target.

Purification:

600 μl of fixation buffer called Binding Buffer in the kit is added to 150 μl of solution containing the converted target. The mixture is deposited on the column supplied in the kit and centrifuged for 30 seconds at 10 000×g. A volume of 100 μl of the Wash Buffer is deposited on the column, which is centrifuged for 30 seconds at 12 000×g.

Desulfonation:

A volume of 200 μl of Desulfonation Buffer is deposited on the same column, which is incubated for 15 minutes at room temperature and then centrifuged for 30 seconds at 12 000×g. The column is then washed twice by adding 200 μl of Wash Buffer and is centrifuged for 30 seconds at 12 000×g.

Elution:

The column is deposited on a clean tube. A volume of 10 μl of elution buffer, called M-Elution Buffer, is deposited at the center of the column, which is centrifuged for 30 seconds at 12 000×g. The 10 μl of eluate contains the DNA converted by the bisulfite, ready to be used for an amplification.

The converted samples of gDNA from *Escherichia coli* are then hydrolyzed with a mixture of Nuclease P1 (13 U) (N8630-1VL, Sigma Aldrich, St Louis, U.S.A.) and of alkaline phosphatase (3 U) (P7923-2KU, Sigma. Aldrich, St Louis, U.S.A.) overnight at 37° C. The hydrolyzed genomic DNA is then analyzed by HPLC.

Conditions for HPLC and Detection by Mass Spectrometry with Electrospray Ionization For this, we use:

a WATERS Alliance 2795 HPLC chain (Milford, Conn. USA), a WATERS XTerra MS C18 column (Milford, Conn., USA) 4.6×30 2.5 μm, used with a flow of 1 ml/minute at 30° C. (detection at 260 nm) with a linear gradient of acetonitrile of: 0% to 5% (4 min); 5% to 12% (5 min); 12% to 90% (2 min) and 90% to 0% (3 min) in 10 mM of ammonium formate at pH 7.

a PDA 996 diode array detector, software Empower version 2 (Milford, Conn., USA), a mass detector (ZQ Electrospray WATERS ((Milford, Conn., USA).

Figure 3A:
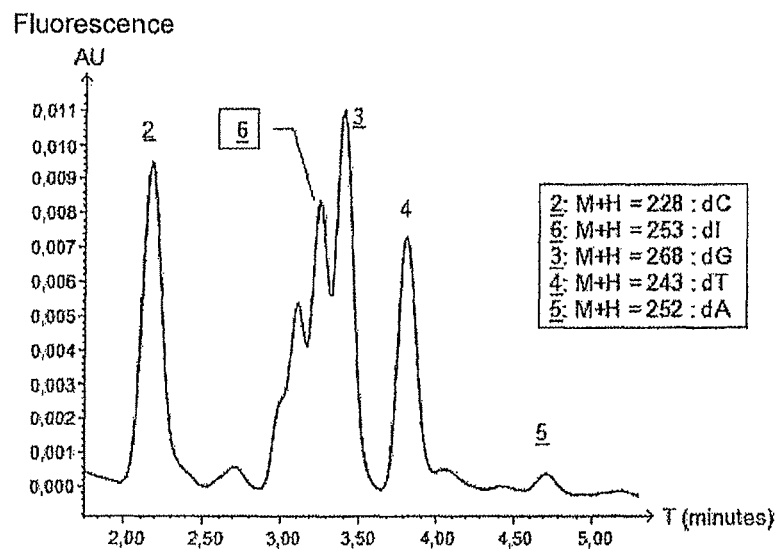

Conclusions:

FIG. 3(*a*) shows the results of analysis of the composition of a hydrolyzed gDNA from *Escherichia coli* not converted with bisulfite, by mass spectrometry with electrospray ionization (ESI). Four main peaks can be seen, corresponding to the four types of nucleosides: deoxyadenosine dA, deoxythimidine dT, deoxyguanosine dG, deoxycytidine dC with a trace of deoxyinosine dI. The deoxyinosine comes from the enzymatic action of adenosine deaminase on deoxyadenosine. Adenosine deaminase is a contaminant that is found at trace levels in commercial preparations of alkaline phosphatase.

Figure 3B:
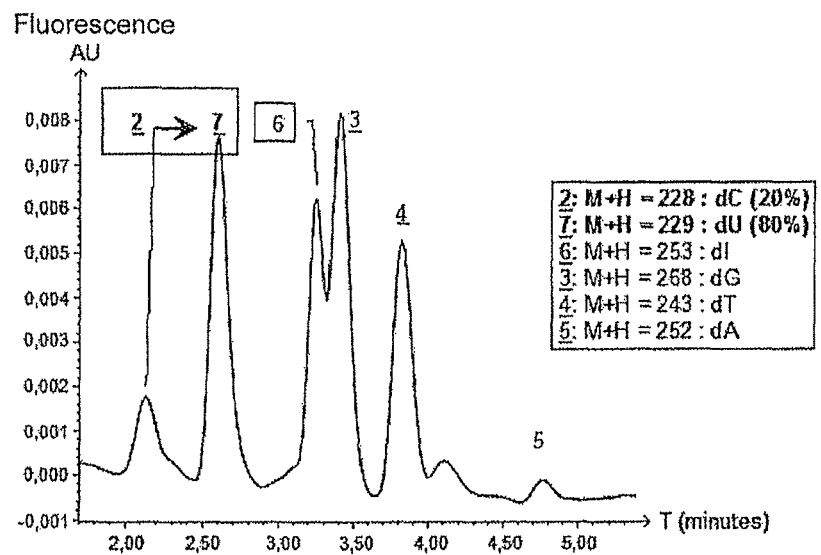

FIG. 3(b) shows the analysis of the composition of a hydrolyzed gDNA from *Escherichia coli* after conversion by bisulfite. There is appearance of a new elution peak (peak 7) corresponding to deoxyuridine dU and quasi-disappearance of the peak of dC (peak 2). The other elution peaks (peaks 3, 4 and 5) are unchanged and correspond to the presence of dG, dT and dA. This chromatogram shows that this DNA is composed of four nucleosides, which are: dU, dA, dT and dG.

In this example, the conversion efficiency in these experimental conditions is 80%. This efficiency is a function of the size of the DNA of interest that is to be treated. The degree of conversion (or level of efficiency) is much higher on a short fragment of DNA. In our experimental conditions here, the DNA treated is genomic DNA from *E. coli*, i.e. a target DNA of great length, quite difficult to denature and convert. However, conversion of the majority of the dCs to dU has therefore been demonstrated.

EXAMPLE 2

Execution of a Eubacterial NASBA Amplification with Four-Base (PNT) or Three-Base (P3B) Amplification Primers from a Dilution Series of Three- or Four-Base Synthetic Oligonucleotides (called C38 and CNT Respectively)

Objective:
To provide proof of concept, i.e. demonstrate that a eubacterial NASBA performed using three-base primers (P3B1 and P3B2) and base probes (S3B) permits amplification and specific detection of a three-base synthetic target without amplifying the natural targets (CNT), such as contaminating bacterial targets.

Detection is effected in real time by means of a four-base detecting probe (SNT) or a three-base detecting probe (S3B).
Procedure:
This test is performed by carrying out a eubacterial NASBA amplification with, on the one hand:
a dilution series of four-base oligonucleotide targets called CNT, four-base primers (called PNT1 and PNT2) and a four-base detecting probe (SNT), the four types of bases being A, T, G and C;
and on the other hand:
a dilution series of three-base oligonucleotide targets called C3B, primers (P3B1 and P3B2) and a 3-base detecting probe (S3B) that can hybridize to C3B.

The dilution series are from 0 to $10^7$ copies of targets per test.

The oligonucleotide targets, the primers and the probes were ordered as they are, without bisulfite conversion, from Eurogentec, Seraing, Belgium) and have the sequences:

Target CNT (SEQ ID No. 8):
5'-TGGAGCATGTGGTTTAATTCGCTACAACTGTCGTCAGCTCGTGTTC
CGCGGGATGTTGGGTTAAGTCCCGCAACGAGCGCAACCCTTATCCT-3', Primers PNT1 (SEQ ID No. 9):
5'-aattctaatacgactcactataggGCGGGACTTAACCCAACATC-3'

Primers PNT2 (SEQ ID No. 10):
5'-GGAGCATGTGGTTTAATTCG-3'

Detecting probe SNT (SEQ ID No. 11):
5'-FAM-cgatcgTWTCGTCAGCTCGTGTcgatcg-Dabcyl-3'
with W = 2'-O-Me-guanosine.

Target C3B (SEQ ID No. 12):
5'-TGGAGTATGTGGTTTAATTTGTTATAATTGTTGTTAGTTTGTGTTT
TGTGGGATGTTGGGTTAAGTTTTGTAATGAGTGTAATTTTTATTTT-3'

Primer P3B1 (SEQ ID No. 13):
5'-aattctaatacgactcactataggACAAAACTTAACCCAACATC-3'

Primer P3B2 (SEQ ID No. 14):
5'-GGAGTATGTGGTTTAATTTG-3'

Detecting probe S3B (SEQ ID No. 15):
5'-FAM-cgatcgTWTTGTTAGTTTGTGTcgatcg-Dabsyl-3'
with W = 2'-O-Me-guanosine.

In these sequences, the sequence of the promoter T7 corresponds to the lower-case letters; as the detecting probe is a molecular beacon, the sequence of the loop is shown as uppercase letters and the sequences of the stems are shown as lower-case letters in bold.

The NASBA amplification is performed following the manufacturer's instructions supplied in the kit NASBA NucliSENS EasyQ HIV-1 v1.2 (Ref. 285 036, bioMérieux, Marcy l'Etoile, France). Briefly, the amplification mixtures (Mix) and the enzyme mixture are prepared as follows:
Amplification mixture (amount for eight tubes):
water of NASBA grade, called NASBA water: 11.2 µl,
reagent diluent: 64 µl,
KCl: 12.8 µl,
sphere of reagents: 1 sphere, and
mixture of primers and probe: 8 µl.
Enzyme mixture (amount for eight tubes):
enzyme diluent: 45 µl (for 8 tubes), and
sphere of enzymes: 1 sphere.
Setup: A volume of 10 µl of amplification mixture is deposited in a 0.2-ml tube, to which a volume of 5 µl of target nucleic acid is added. A volume of 5 µl of enzyme mixture is deposited in the stopper of the tube. The tube is closed and incubated for 5 minutes at 65° C. and then for 5 minutes at 41° C. The tube is briefly centrifuged, without stirring, to combine the two mixtures and then incubated in a NucliSens EasyQ fluorometer (Ref. 200309, bioMérieux, Marcy l'Etoile, France) for 90 minutes at 41° C. (standard program QL1-90). The fluorescence is read at 488 nm during the reaction.

Figure 4:
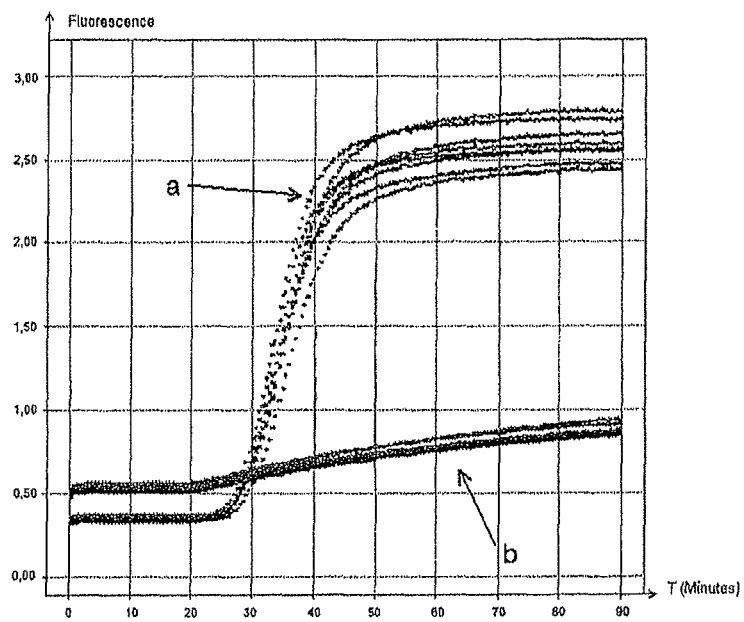
Figure 5:
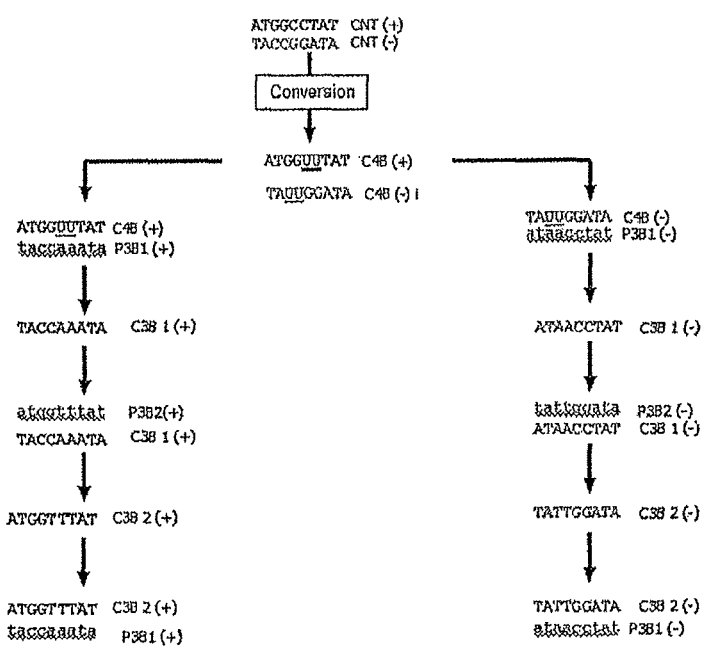
FIG. 5 is a schematic representation of amplification by PCR according to the principle of the invention when the converted target is a double-stranded DNA. Two primer pairs P3B are required for carrying out this amplification.

It is found that NASBA amplification of the target CNT, corresponding to FIG. 4, curves (a), amplifies the contaminating nucleic acids very strongly whereas the signal remains very weak in FIG. 4, curves (b), in the case of a NASBA amplification of the four-base target. This proves that there is little if any amplification of the contaminants by the primers P3B1 and P3B2, and there is little if any detection of them by the probe S3B.

FIG. 6A shows that NASBA amplification performed with the primers PNT1 and PNT2 does not allow the specific target CNT to be differentiated (at concentrations from 0 to $10^7$ copies per test) from the negative control (0 copy per test). Conversely, NASBA amplification performed with the primers P3B1 and P3B2 on a three-base target C3B (FIG. 6B) gives a dilution series of the specific target C3B with a good sensitivity of detection. In this example, the sensitivity is $10^3$ copies per test.

Conclusions:

This experiment clearly shows the advantage offered by this amplification on three-base targets, as it permits a gain in detection sensitivity of targets of about four log. In experiment of NASBA amplification of the target CNT, the negative control is identified with a signal corresponding to about $10^{e}7$ copies/test whereas this signal is below $10^{e}3$ copies/test in NASBA amplification of the target C3B.

EXAMPLE 3

Execution of a Eubacterial PCR Amplification with PNT or P3B Primers from a Dilution Series of Three- or Four-Base Synthetic Oligonucleotide Targets Objective:

To demonstrate the gain in sensitivity of detection of a three-base synthetic bacterial target (C3B) after amplification by eubacterial PCR using three-base primers (P3B) specific to the three-base targets (C3B) relative to an amplification by eubacterial PCR on a natural target (CNT) with four-base primers (PNT) and a four-base probe (SNT).

Procedure:

Eubacterial PCR amplification is performed using fluorescent detection primers and probes called Taqman®, SNT or S3B. The targets are synthetic oligonucleotides of 92 nucleotides having a four-base sequence (A, T, G, C for CNT; SEQ ID No. 8) or three-base sequence (A, T, G for C3B; SEQ ID No. 12). The amplifications are carried out on dilutions of targets varying from 0 to $10^5$ copies per test.

Amplification is performed according to the manufacturer's instructions supplied in the kit Roche LightCycler Fast-Start DNA Master Hyprobe, #030003248001 (Basle, Switzerland). The sequences of the primers and probe used are as follows:

PCR on a natural target, target CNT:

```
Primer PNT1a (SEQ ID No. 16):
5'-AGGATAAGGGTTGCGCTCGTTGCGGG-3'

Primer PNT2a(SEQ ID NO. 17):
5'-TGGAGCATGTGGTTTAATTC-3'

Probe TaqMan ® SNTa (SEQ ID NO. 18):
5'-FAM-TWTCGTCAGCTCGTGT-BHQ1-3'
with W = 2'-OMe-G
```

PCR on a three-base target, target C3B:

```
Primer P3B1a (SEQ ID No. 19):
5'-AAAATAAAAATTACACTCATTACAAA-3'

Primer P3B2a (SEQ ID No. 20):
5'-TGGAGTATGTGGTTTAATTT-3'

Probe TaqMan ® S3Ba (SEQ ID No. 21):
5'-FAM-TGTTGYYKWYYYGTGT-BHQ1-3'
with Y = 2'-OMe-U, W = 2'-OMe-G and K = 2'-OMe-A.
```

The nucleotides 2'-O—Me make it possible to compensate the loss of hybridization temperature connected with the disappearance of the C bases in the sequences of the three-base probes. The point introduction of uracil (in this instance, modified uracil) in the design of this TaqMan® probe makes it possible to improve hybridization with the amplicons.

Amplification mixture: (for one tube)
Water for PCR: 10.4 µl,
Primer P1 (10 µM): 1 µl,
Primer P2 (10 µM): 1 µl,
Probe (2.5 µM): 2 µl,
$MgCl_2$ (25 mM): 1.6 µl, and
Amplification mixture (10× Master Mix): 2 µl.

The final amplification mixture is pre-incubated at 95° C. for 10 minutes, then amplified in 45 cycles made up of stages of denaturation at 95° C. for 10 seconds, hybridization at 50° C. for 15 seconds and elongation at 60° C. for 15 seconds. Amplification is stopped by incubation for 5 minutes at 95° C. The fluorescence is read at 530 nm, during the elongation cycle.

FIG. 7A shows that below $10^3$ copies of CNT targets per test, the PCR signal cannot be differentiated from the signal of the negative control (0 copies). The sensitivity of a eubacterial PCR on a CNT target is therefore $10^3$ copies per test.

In FIG. 7B, eubacterial PCR amplification on three-base oligonucleotide targets (C3B) shows excellent sensitivity with a curve that remains horizontal for the negative control (0 copy per test) and sensitivity greater than 10 copies per test.

Conclusions:

This experiment demonstrates that using eubacterial PCR amplification on three-base synthetic targets C3B gives a gain in sensitivity of four log.

The sensitivity of amplification of a three-base target is independent of the amplification technique and of the means of detection used. These experiments show that regardless of the amplification technique and the form of the three-base detecting probes used, the sensitivity of amplification of a three-base target according to the invention is far greater than that of a conventional amplification of a natural target (CNT).

EXAMPLE 4

Demonstration of the Gain in Sensitivity Provided by Conversion of the Bacterial DNA Target and PCR Amplification Using P3B Primers Objective:

After demonstration on a synthetic model (examples 2 and 3), an assay is performed on a real biological model converted experimentally by bisulfite. The objective is to demonstrate the gain in sensitivity of detection of a bacterial target that is converted and then amplified by PCR using P3B amplification primers specific to the converted targets.

Procedure:

This demonstration is performed using a commercial conversion kit Zymo Research and according to the instructions of the supplier of the kit (cf. example 1). The conversion is performed on extract of genomic DNA from *Escherichia coli* (O157, Sigma IRMM449-1EA) composed of nucleic acids of 50 to 4000 nucleotides. The eubacterial PCR amplifications are carried out in the same experimental conditions as those described in example 3, with the same primers and the same detecting probes. The fluorescence is read at 530 nm during the elongation cycle.

FIG. 8A corresponds to the experimental conditions in which the target DNA from *E. coli* has not been treated with bisulfite. This DNA is therefore constituted of a nucleotide sequence with four different types of bases, namely A, T, G and C. Amplification of this DNA generates amplicons constituted of a sequence of four different types of bases (A, T, G and C).

FIG. 8B corresponds to the experimental conditions in which DNA from *E. coli* was converted after treatment with bisulfite. This converted DNA (4-base converted target) is composed of a nucleotide sequence with four different types of bases, namely A, T, G, U. Amplification of this DNA converted with the primers according to the invention (3-base primers) will generate amplicons constituted of a nucleotide sequence with three different types of bases: A, T, C or A, T, G.

As indicated in FIG. 8A, in the case of a eubacterial PCR amplification of an unconverted DNA from *Escherichia coli*, the level of sensitivity is 1000 Ceq per test. The negative control at 0 Ceq per test is confused with the 100 Ceq per test. This figure shows that below a threshold of 100 000 copies of a target DNA, it is not possible to distinguish the target DNA from the contaminating DNAs present in the various reagents used.

FIG. 8B shows that after conversion of the sample by bisulfite and eubacterial PCR amplification, the level of sensitivity obtained is from 0.1 to 1 Ceq per test. The negative control gives a very weak signal. This experiment demonstrates that the method according to the invention makes it possible to evade all contaminating elements and thus obtain a very significant gain in sensitivity.

Moreover, although the efficiency of conversion of the genomic DNA from *E. coli* in our experimental conditions is 80% (see above), the sensitivity of detection is relatively high and does not appear to be affected by the 20% of genomic DNA from *E. coli* that was not converted. As this 20% of genomic DNA has not been altered at the level of its types of bases, it becomes ipso facto contaminating and is not amplified by the method of the invention.

CONCLUSIONS

This example of eubacterial PCR amplification on a target of bacterial DNA converted by bisulfite clearly demonstrates the gain in sensitivity that this treatment of the sample can provide. In fact, the gain in sensitivity is of four log. By employing amplification with preliminary treatment with bisulfite, the signals from the negative controls can be turned off; even if the level of efficiency of the conversion treatment is not close to 100%.

It is therefore a method of choice for completely evading the bacterial contaminating elements present in the extraction, purification and amplification reagents.

The invention claimed is:

1. A method of specifically amplifying a nucleic acid of interest, comprising:

treating a biological sample chemically or enzymatically to permit conversion of one type of nucleic acid base to another type of base, the biological sample being selected from the group consisting of tissue, blood, serum, saliva, circulating cells of a patient, a food product, an agricultural product, and an environmental product;

adding amplification primers and amplification reagents to the biological sample, each primer being constituted of three different types of bases and being specific to a converted nucleic acid of interest or to a nucleic acid that is complementary to the converted nucleic acid of interest, the primers comprising at least one modified nucleotide selected from the group consisting of alpha-oligonucleotides, PNAs, LNAs, and 2'-O-alkyl ribonucleotides; and amplifying the converted nucleic acid of interest provided that the nucleic acid of interest was present in the biological sample, wherein amplification of contaminating nucleic acids is circumvented by converting the one type of nucleic acid base to another type of base prior to adding the amplification reagents, which are a source of contaminating nucleic acids, to the biological sample.

2. A method of specifically detecting a nucleic acid of interest, comprising:

treating a biological sample chemically or enzymatically to permit conversion of at least one type of nucleic acid base to another type of base, the biological sample being selected from the group consisting of tissue, blood, serum, saliva, circulating cells of a patient, a food product, an agricultural product, and an environmental product;

adding amplification primers, at least one detecting probe, and amplification reagents to the biological sample, each primer and probe being constituted of three different types of bases, the primers comprising at least one modified nucleotide selected from the group consisting of alpha-oligonucleotides, PNAs, LNAs, and 2'-O-alkyl ribonucleotides;

amplifying a converted nucleic acid of interest to obtain amplicons provided that the nucleic acid of interest was present in the biological sample; and detecting any amplicons obtained as a result of amplification, wherein:

each primer is specific to the converted nucleic acid of interest or to a nucleic acid that is complementary to the converted nucleic acid of interest and each probe is complementary to an amplicon; and amplification of contaminating nucleic acids is circumvented by converting the one type of nucleic acid base to another type of base prior to adding the amplification reagents, which are a source of contaminating nucleic acids, to the biological sample.

3. The method as claimed in claim 1, wherein the primers comprise at least one 2'-O-methyl ribonucleotide.

4. The method as claimed in claim 2, wherein the primers comprise at least one 2'-O-methyl ribonucleotide.

5. The method as claimed in claim 1, wherein the biological sample is chemically treated with a sulfur-containing chemical.

6. The method as claimed in claim 5, wherein the sulfur-containing chemical includes a bisulfite ion ($HSO_3^-$).

7. The method as claimed in claim 1, wherein the biological sample is enzymatically treated with a cytosine deaminase.

8. The method as claimed in claim 1, wherein the chemical or enzymatic treatment converts one type of nucleic acid base to uracil (U).

9. The method as claimed in claim 1, wherein the chemical or enzymatic treatment converts cytosine (C) to uracil (U).

10. The method as claimed in claim 9, wherein a first primer, hybridizing to the converted nucleic acid of interest, is formed from adenine(s) (A), cytosine(s) (C) and/or thymine(s) (T), and a second primer, hybridizing to the strand resulting from the elongation of said first primer, is formed from adenine(s) (A), guanine(s) (G) and/or thymine(s) (T).

11. The method as claimed in claim 1, wherein the biological sample is enzymatically treated with an adenosine deaminase.

12. The method as claimed in claim 11, wherein the adenosine deaminase converts adenine (A) to hypoxanthine.

13. The method as claimed in claim 11, wherein a first primer, hybridizing to the converted nucleic acid of interest, is formed from adenine(s) (A), cytosine(s) (C) and/or guanine(s) (G), and a second primer, hybridizing to the strand resulting from the elongation of said first primer, is formed from cytosine(s) (C), guanine(s) (G) and/or thymine(s) (T).

14. The method as claimed in claim 1, wherein the amplification is an RT-PCR amplification.

15. The method as claimed in claim 1, wherein the amplification is a single-stranded PCR amplification.

16. The method as claimed in claim 1, wherein the amplification is a double-stranded PCR amplification.

17. The method as claimed in claim 16, wherein amplification is effected by means of two pairs of amplification primers specific to each strand of the converted nucleic acid of interest.

18. The method as claimed in claim 1, wherein the amplification is a post-transcriptional amplification.

19. The method as claimed in claim 1, wherein the nucleic acid of interest is a deoxyribonucleic acid (DNA) and/or a ribonucleic acid (RNA).

20. The method as claimed in claim 1, wherein the nucleic acid of interest is selected from the group consisting of eubacterial, fungal, viral, and yeast targets.

21. The method as claimed in claim 2, wherein the amplification primers are specific to a bacterial genus and the at least one detecting probe is specific to at least one bacterial species.

22. The method as claimed in claim 1, further comprising purifying the treated biological sample before adding the amplification primers and amplification reagents to the treated biological sample.

23. The method as claimed in claim 2, further comprising purifying the treated biological sample before adding the amplification primers, at least one detecting probe, and amplification reagents to the treated biological sample.

24. The method as claimed in claim 22, wherein the purification comprises performing column filtration, desulfonation in a basic medium, and elution through a column.

25. The method as claimed in claim 23, wherein the purification comprises performing column filtration, desulfonation in a basic medium, and elution through a column.

* * * * *

SEQUENCE LISTING

```
<160> NUMBER OF SEQ ID NOS: 21

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct-target

<400> SEQUENCE: 1
atcgaaattt cccgggatcg                                                    20

<210> SEQ ID NO 2
<211> LENGTH: 20
<212> TYPE: DNA
<213> ORGANISM: Artificial Sequence
<220> FEATURE:
<223> OTHER INFORMATION: This sequence is a combined DNA/RNA sequence
<220> FEATURE:
<223> OTHER INFORMATION: Synthetic Construct-converted target
<220> FEATURE:
<221> NAME/KEY: misc_feature
<222> LOCATION: (3)..(3)
<223> OTHER INFORMATION: n is uracil
<220> FEATURE:
<221> NAME/KEY: misc_feature
<222> LOCATION: (11)..(11)
<223> OTHER INFORMATION: n is uracil
<220> FEATURE:
<221> NAME/KEY: misc_feature
<222> LOCATION: (12)..(12)
<223> OTHER INFORMATION: n is uracil
<220> FEATURE:
<221> NAME/KEY: misc_feature
<222> LOCATION: (13)..(13)
<223> OTHER INFORMATION: n is uracil
<220> FEATURE:
<221> NAME/KEY: misc_feature
<222> LOCATION: (19)..(19)
<223> OTHER INFORMATION: n is uracil

<400> SEQUENCE: 2
atngaaattt nnngggatng                                                    20

<210> SEQ ID NO 3
<211> LENGTH: 4
<212> TYPE: DNA
```

```
<213> ORGANISM: Artificial Sequence
<220> FEATURE:
<223> OTHER INFORMATION: Synthetic Construct-primer

<400> SEQUENCE: 3 caat                                                                    4

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct-amplicon

<400> SEQUENCE: 4
caatcccaaa aaatttcaat                                                  20

<210> SEQ ID NO 5
<211> LENGTH: 4
<212> TYPE: DNA
<213> ORGANISM: Artificial Sequence
<220> FEATURE:
<223> OTHER INFORMATION: Synthetic Construct-primer

<400> SEQUENCE: 5 attg                                                                    4

<210> SEQ ID NO 6
<211> LENGTH: 6
<212> TYPE: DNA
<213> ORGANISM: Artificial Sequence
<220> FEATURE:
<223> OTHER INFORMATION: Synthetic Construct-probe

<400> SEQUENCE: 6 aaaaaa                                                                  6

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct-amplicon

<400> SEQUENCE: 7
attgaaattt tttgggattg                                                  20

<210> SEQ ID NO 8
<211> LENGTH: 92
<212> TYPE: DNA
<213> ORGANISM: Artificial Sequence
<220> FEATURE:
<223> OTHER INFORMATION: Synthetic Construct-target

<400> SEQUENCE: 8
tggagcatgt ggtttaattc gctacaactg tcgtcagctc gtgttccgcg ggatgttggg       60
ttaagtcccg caacgagcgc aacccttatc ct                                    92

<210> SEQ ID NO 9
<211> LENGTH: 44
<212> TYPE: DNA
<213> ORGANISM: Artificial Sequence
<220> FEATURE:
<223> OTHER INFORMATION: Synthetic Construct-promoter + primer

<400> SEQUENCE: 9
```
aattctaata cgactcacta tagggcggga cttaacccaa catc    44

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct-primer

<400> SEQUENCE: 10
ggagcatgtg gtttaattcg    20

<210> SEQ ID NO 11
<211> LENGTH: 28
<212> TYPE: DNA
<213> ORGANISM: Artificial Sequence
<220> FEATURE:
<223> OTHER INFORMATION: Synthetic Construct-probe
<220> FEATURE:
<221> NAME/KEY: misc_feature
<222> LOCATION: (8)..(8)
<223> OTHER INFORMATION: g = 2'-O-methyl-guanosin

<400> SEQUENCE: 11
cgatcgtgtc gtcagctcgt gtcgatcg    28

<210> SEQ ID NO 12
<211> LENGTH: 92
<212> TYPE: DNA
<213> ORGANISM: Artificial Sequence
<220> FEATURE:
<223> OTHER INFORMATION: Synthetic Construct-target

<400> SEQUENCE: 12
tggagtatgt ggtttaattt gttataattg ttgttagttt gtgttttgtg ggatgttggg    60
ttaagttttg taatgagtgt aattttttatt tt    92

<210> SEQ ID NO 13
<211> LENGTH: 44
<212> TYPE: DNA
<213> ORGANISM: Artificial Sequence
<220> FEATURE:
<223> OTHER INFORMATION: Synthetic Construct-promoter + primer

<400> SEQUENCE: 13
aattctaata cgactcacta taggacaaaa cttaacccaa catc    44

<210> SEQ ID NO 14
<211> LENGTH: 20
<212> TYPE: DNA
<213> ORGANISM: Artificial Sequence
<220> FEATURE:
<223> OTHER INFORMATION: Synthetic Construct-primer

<400> SEQUENCE: 14
ggagtatgtg gtttaatttg    20

<210> SEQ ID NO 15
<211> LENGTH: 28
<212> TYPE: DNA
<213> ORGANISM: Artificial Sequence
<220> FEATURE:
<223> OTHER INFORMATION: Synthetic Construct-probe
<220> FEATURE:
<221> NAME/KEY: misc_feature
<222> LOCATION: (8)..(8)

<223> OTHER INFORMATION: g = 2'-O-methyl-guanosin

<400> SEQUENCE: 15
cgatcgtgtt gttagtttgt gtcgatcg                                           28

<210> SEQ ID NO 16
<211> LENGTH: 26
<212> TYPE: DNA
<213> ORGANISM: Artificial Sequence
<220> FEATURE:
<223> OTHER INFORMATION: Synthetic Construct-primer

<400> SEQUENCE: 16
aggataaggg ttgcgctcgt tgcggg                                             26

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct-primer

<400> SEQUENCE: 17
tggagcatgt ggtttaattc                                                    20

<210> SEQ ID NO 18
<211> LENGTH: 16
<212> TYPE: DNA
<213> ORGANISM: Artificial Sequence
<220> FEATURE:
<223> OTHER INFORMATION: Synthetic Construct-probe
<220> FEATURE:
<221> NAME/KEY: misc_feature
<222> LOCATION: (2)..(2)
<223> OTHER INFORMATION: g = 2'-O-methyl-guanosin

<400> SEQUENCE: 18
tgtcgtcagc tcgtgt                                                        16

<210> SEQ ID NO 19
<211> LENGTH: 26
<212> TYPE: DNA
<213> ORGANISM: Artificial Sequence
<220> FEATURE:
<223> OTHER INFORMATION: Synthetic Construct-primer

<400> SEQUENCE: 19
aaaataaaaa ttacactcat tacaaa                                             26

<210> SEQ ID NO 20
<211> LENGTH: 20
<212> TYPE: DNA
<213> ORGANISM: Artificial Sequence
<220> FEATURE:
<223> OTHER INFORMATION: Synthetic Construct-primer

<400> SEQUENCE: 20
tggagtatgt ggtttaattt                                                    20

<210> SEQ ID NO 21
<211> LENGTH: 16
<212> TYPE: DNA
<213> ORGANISM: Artificial Sequence
<220> FEATURE:
<223> OTHER INFORMATION: This sequence is a combined DNA/RNA sequence
<220> FEATURE:
<223> OTHER INFORMATION: Synthetic Construct-probe

```
<220> FEATURE:
<221> NAME/KEY: misc_feature
<222> LOCATION: (6)..(6)
<223> OTHER INFORMATION: u = 2'-O-methyl-uracil
<220> FEATURE:
<221> NAME/KEY: misc_feature
<222> LOCATION: (7)..(7)
<223> OTHER INFORMATION: u = 2'-O-methyl-uracil
<220> FEATURE:
<221> NAME/KEY: misc_feature
<222> LOCATION: (8)..(8)
<223> OTHER INFORMATION: a = 2'-O-methyl-adenin
<220> FEATURE:
<221> NAME/KEY: misc_feature
<222> LOCATION: (9)..(9)
<223> OTHER INFORMATION: g = 2'-O-methyl-guanosin
<220> FEATURE:
<221> NAME/KEY: misc_feature
<222> LOCATION: (10)..(10)
<223> OTHER INFORMATION: u = 2'-O-methyl-uracil
<220> FEATURE:
<221> NAME/KEY: misc_feature
<222> LOCATION: (11)..(11)
<223> OTHER INFORMATION: u = 2'-O-methyl-uracil
<220> FEATURE:
<221> NAME/KEY: misc_feature
<222> LOCATION: (12)..(12)
<223> OTHER INFORMATION: u = 2'-O-methyl-uracil

<400> SEQUENCE: 21
tgttguuagu uugtgt                                               16
```